United States Patent [19]

Schoen et al.

[11] Patent Number: 4,879,299

[45] Date of Patent: Nov. 7, 1989

[54] TREATMENT OF HEART CONDITIONS WITH SPARTEIN COMPOUNDS

[75] Inventors: Uwe Schoen, Burgdorf; Wolfgang Kehrbach, Hanover; Bernd Hachmeister, Isernhagen; Gerd Buschmann, Hanover; Ulrich G. Kuehl, Gehrden, all of Fed. Rep. of Germany

[73] Assignee: Kali-Chemie Pharma GmbH, Hanover, Fed. Rep. of Germany

[21] Appl. No.: 135,109

[22] Filed: Dec. 18, 1987

Related U.S. Application Data

[63] Continuation-in-part of Ser. No. 875,311, Jun. 17, 1986, Pat. No. 4,755,520.

[30] Foreign Application Priority Data

Jun. 22, 1985 [DE] Fed. Rep. of Germany ....... 3522475
Dec. 19, 1986 [DE] Fed. Rep. of Germany ....... 3643402

[51] Int. Cl.$^4$ .................. A61K 31/435; C07D 471/22
[52] U.S. Cl. ...................................... 514/286; 546/63
[58] Field of Search ........................... 546/63; 514/286

[56] References Cited

U.S. PATENT DOCUMENTS 4,755,520 7/1988 Schön et al. ........................ 546/63

FOREIGN PATENT DOCUMENTS 3522475 6/1985 Fed. Rep. of Germany .

OTHER PUBLICATIONS

Burger, Med. Chem. 2nd Ed., p. 42 (1960).
Rink et al, Chem. Abs., vol. 51, No. 11, 8114 (1958).

Primary Examiner—Mukund J. Shah
Assistant Examiner—Andrew G. Rozycki
Attorney, Agent, or Firm—Foley & Lardner, Schwartz, Jeffery, Schwaab, Mack, Blumenthal & Evans

[57] ABSTRACT

Compounds of Formula (I)

$$S-(CH_2)_n-Atm \quad (I)$$

in which
S is a 17-spartein nucleus,
n is 0 or 1, and
A is 2-furyl, 2-thienyl or 2-(N-loweralkyl)pyrryl
when n=0, or
3-furyl or 3-thienyl when n=1, or pyridyl, or a phenyl group of Formula (II)

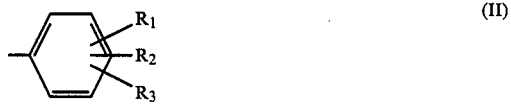

in which at least one of $R_1$, $R_2$ and $R_3$ is a defined substituent other than hydrogen. Such compounds and corresponding compounds in which A is an unsubstituted phenyl group are useful in pharmaceutical compositions as heart affecting agents. Methods of preparing such compounds and pharmaceutical compositions are disclosed. Also described is the use of such compounds or compositions, particularly compounds or compositions with positive inotropic activity, to treat various heart conditions.

11 Claims, No Drawings

TREATMENT OF HEART CONDITIONS WITH SPARTEIN COMPOUNDS

Cross-Reference to Related Applications

This application is a continuation-in-part of our copending U.S. patent application Ser. No. 875,311 filed June 17, 1986.

BACKGROUND OF THE INVENTION

This invention relates to new aromatic compounds of the spartein series, to their use and to methods for their preparation. It also relates to medicaments which contain such compounds and to methods for the preparation of such medicaments. In one particular aspect the invention also relates to use of 17-substituted spartein derivatives, especially 17-benzyl and substituted benzyl spartein derivatives, with positive inotropic activity to treat ischemic and non-ischemic cardiac insufficiencies, and to the production of suitable pharmaceutical compositions for such treatments.

Spartein, an alkaloid which can be extracted from broom (*Cvtisus scoparius*), and its properties, which affect the heart and in particular influence the heart rhythm, have already been described in the technical literature.

An increase in effect with regard to extension of the refractory period can be achieved with sparteins substituted in position 17 by alkyl, i.e. compounds which have the following structure:

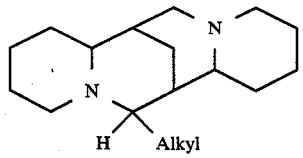

Such compounds are described in DE-OS 23 60 475. Also, a dimeric spartein with antiarrhythmic effect, 17,17'-bisspartein, is described in published European patent application No. EP 46,565.

The compounds of the prior art display good properties in the treatment of heart rhythm complaints, but their activity patterns could still be improved upon.

The most widely known medicines with positive inotropic activity are heart glycosides (digitalis products and strophantin products). In addition to their positive inotropic activity which increases the beat volume they also lead indirectly to a decrease of the heart frequency through accommodation to the increased beat volume. The great disadvantage of the heart glycosides lies in their extraordinarily narrow therapeutic range, which is particularly limited by the heart arrhythmia inducing side effects of these preparations.

All other positive inotropically active medicines have the disadvantage that they do not decrease the heart frequency and in many cases even produce an increase in the heart frequency. This leads to an increased stress on the heart which is particularly undesirable in cases of insufficient heart pumping function.

SUMMARY OF THE INVENTION

It is an object of the invention to provide new spartein derivatives with a modified activity pattern.

It is also an object of the invention to provide new positive inotropically active pharmaceutical preparations with improved activity profiles for treating heart disorders.

These and other objects of the invention are achieved by providing an aromatic compound corresponding to the Formula (I)

$$S-(CH_2)_n-A \qquad (I)$$

in which
S is a 17-spartein nucleus,
n is 0 or 1, and
A is 2-furyl, 2-thienyl or 2-(N-alkyl)-pyrryl when n=0, or
3-furyl or 3-thienyl when n=1, or
pyridyl, or
substituted phenyl of Formula (II)

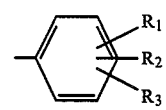

in which $R_1$, $R_2$ and $R_3$ are independently selected from the group consisting of hydrogen, alkyl, alkoxy, fluorine, chlorine, bromine, trifluoromethyl,

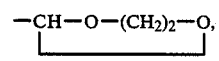

hydroxy, or $-CO-R_4$ in which $R_4$ is hydrogen, alkoxy, hydroxy, amino or substituted amino, or two adjacent ones of $R_1$, $R_2$ and $R_3$ together form an alkylene dioxy group; at least one of $R_1$, $R_2$ and $R_3$ being other than hydrogen; or a pharmacologically usable acid addition salt thereof.

In other aspects of the invention, the objects are achieved by providing methods of producing the aforedescribed compounds, pharmaceutical compositions comprising such compounds or corresponding compounds in which A represents an unsubstituted phenyl group and methods of preparing such pharmaceutical compositions.

DETAILED DESCRIPTION OF PREFERRED EMBODIMENTS

According to one aspect of the present invention there is provided an aromatic compound of the general Formula (I)

$$S-(CH_2)_n-A \qquad (I)$$

in which
S is a 17-spartein nucleus or group,
n is 0 or 1, and
A is:
(a1) 2-furyl, 2-thienyl or 2-(N-alkyl) pyrryl when n=0, or
(a2) 3-furyl or 3-thienyl when n=1, or
(b) pyridyl, or
(c) substituted phenyl of Formula (II)

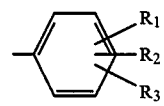

in which, independently of each other, one or two of the groups $R_1$ to $R_3$ may be hydrogen and from at least one up to three of the groups $R_1$ to $R_3$ are independently selected from the group consisting of (c1) alkyl
(c2) alkoxy
(c3) fluorine
(c4) chlorine
(c5) bromine
(c6) trifluoromethyl
(c7) two adjacent groups together forming alkylene dioxy (c8) $-CH-O-(CH_2)_2-O$ 

(c9) hydroxy
(c10) $-CO-R_4$ in which $R_4$ is hydrogen, alkoxy, hydroxy, amino or substituted amino; or a pharmacologically usable acid addition salt thereof. Where A is a pyridyl group, this may be a 2-, 3-or 4-pyridyl group; preferably a 2- or 4-pyridyl group. Where a substituent group is an alkyl group, this may be a straight chain or branched alkyl group and is preferably a lower alkyl group, that is to say an alkyl group with up to four carbon atoms. Preferred branched alkyl radicals, therefore, include isopropyl, sec.-butyl and (2-methylpropyl) groups, while the preferred straight chain groups are the methyl, ethyl, n-propyl and n-butyl group.

Where a substituent group is an alkoxy group, it is preferably a lower alkoxy group, such as a methoxy, ethoxy, propoxy or butoxy group.

Where a substituent group is an alkylene dioxy group, it is preferably the group $-O-(CH_2)_q-O-$ where q is 1 or 2.

According to one embodiment of the invention, none of the radicals $R_1$ to $R_3$ is a hydrogen atom. The corresponding compounds will be referred to hereinafter as "trisubstituted". An example of such a compound in the case where n=1 is the substitution 3,4,5-trimethoxy.

In another embodiment of the invention, one of the radicals $R_1$ to $R_3$ is a hydrogen atom. Such compounds are referred to as "disubstituted". Examples of such compounds in the case where n=1 are the substitutions 2,4-dimethyl, 2,3-dimethoxy, 2,4-dichloro, 2,6-dichloro, 3,5-dichloro, 2-fluoro-3-methyl, 2,6-difluoro, 2-fluoro-6-chloro and 3-methoxy-4-formyl.

A particular case of disubstitution is where two adjacent groups $R_1$ to $R_3$ together form an alkylene dioxy group. Examples of such compounds in the case where n=1 are the substituents 3,4-methylene dioxy and 3,4-ethylene dioxy.

In a further embodiment of the invention, two of the groups $R_1$ to $R_3$ are hydrogen atoms. Such compounds are referred to as "monosubstituted". The substituent in such a case may be in the ortho, meta or para position with respect to the connection with the spartein nucleus. If n=0 in Formula (I), monosubstituted compounds of the Formula (Vm)

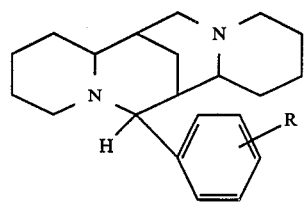

are preferred, in which R is a 3-methyl, 2-methoxy, 3-methoxy, 4-methoxy, 4-hydroxy, 2-trifluoromethyl, 3-trifluoromethyl, 4-trifluoromethyl, 3-fluoro, 4-fluoro, 3-chloro, 4-chloro, 4-bromo or 3-formyl group.

If n =1 in Formula (I), monosubstituted compounds of the Formula (VIm)

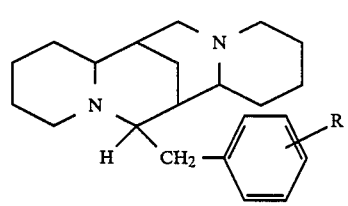

are preferred, in which R is a 2-methyl, 3-methyl, 4-methyl, 2-methoxy, 3-methoxy, 4-methoxy, 3-hydroxy, 2-fluoro, 3-fluoro, 4-fluoro, 2-chloro, 3-chloro, 4-chloro, 2-bromo, 3-bromo, 4-bromo, 3-trifluoromethyl, 4-formyl or 4-(N,N-diisopropyl)-aminocarbonyl group.

Those compounds of Formula (I) in which n is 1 are particularly preferred.

The invention also comprises medicaments or pharmaceutical compositions which contain at least one of the aforementioned compounds of Formula (I) or a pharmaceutically acceptable addition salt thereof.

In accordance with a preferred aspect of the invention, 17-phenylspartein and 17-benzylspartein derivatives corresponding to the Formula (I)

$$S-(CH_2)_n-A \qquad (I)$$

in which n=0 or 1 and A represents a phenyl group of the Formula (II)

in which $R_1$, $R_2$ and $R_3$ have the meanings given above or their pharmaceutically acceptable acid addition salts are used as active agents to produce pharmaceutical compositions suitable for treating heart disorders in humans and large mammals. 17-benzylspartein derivatives (i.e. compounds in which n=1) wherein $R_1$, $R_2$ and $R_3$ individually represent hydrogen, lower alkyl, lower alkoxy, halogen, trifluoromethyl or hydroxy are particularly preferred, as are also such compounds in which two of the groups $R_1$ and $R_2$ are bound to adjacent carbon atoms and together represent an alkylene dioxy group with 1 or 2 carbon atoms.

It has now surprisingly been found that the compounds of Formula I are distinguished by a novel activity profile on the heart and, in addition to heart frequency decreasing and antiarrhythmic characteristics, also exhibit marked positive inotropic activity.

The combination of positive inotropic activity, i.e. ability to increase the contracting force of the heart, with a heart frequency decreasing activity component leads to economies in heart effort. Despite an increase in the pumping volume, no corresponding increase occurs in the oxygen demand of the heart. This is an extraordinarily desirable combination of activities for treating heart failure or insufficient heart pumping function which previously has not been achieved with positive inotropic pharmaceuticals which do not belong to the heart glycosides, and it represents a significant advantage in the treatment of heart failure or insufficient heart pumping function.

The compounds of the invention are also distinguished by a broad therapeutic range, and even at high doses they have no arrhythmogenic side effects.

In the particularly preferred compounds or compositions of the invention, the lower alkyl groups may be straight chain or branched alkyl groups with 1 to 4, preferably 1 or 2 carbon atoms, most preferably methyl groups. The lower alkoxy groups may likewise be straight chain or branched groups containing 1 to 4, preferably 1 or 2, carbon atoms, most preferably methoxy groups. Suitable halogen substituents include fluorine, chlorine or bromine. Examples of monosubstituted compounds include those compounds in which $R_2$ and $R_3$ represent hydrogen and $R_1$ has any of the following meanings: 2-methyl, 3-methyl, 4-methyl, 2-methoxy, 3-methoxy, 4-methoxy, 3-hydroxy, 2-fluoro, 3-fluoro, 4-fluoro, 2-chloro, 3-chloro, 4-chloro, 2-bromo, 3-bromo, 4-bromo, or 3-trifluoromethyl. Examples of disubstituted compounds include those in which $R_3$ represents hydrogen and $R_1$ and $R_2$ stand for 2,4-dimethyl, 2,3-dimethoxy, 3,4-dichloro, 2,6-dichloro, 3,5-dichloro, 2-fluoro-3-methyl, 2,6-difluoro, 2-fluoro-6-chloro. An example of a trisubstituted compound is the 3,4,5-trimethoxy compound.

Suitable pharmacologically usable acid addition salts of the compounds of Formula (I) include watersoluble and water-insoluble salts of inorganic and organic acids, and specific examples of such salts include the hydrochloride, hydrobromide, hydroiodide, phosphate, nitrate, sulfate, perchlorate, acetate, citrate, gluconate, benzoate, propionate, butyrate, salicylate, sulphosalicylate, maleinate, laurate, fumarate, succinate, oxalate, tartrate, stearate, tosylate (p-toluene sulfonate), 2-hydroxy-3-naphthoate, 3-hydroxy-2-naphthoate, mesylate (methane sulfonate) and naphthalene sulfonate The invention further comprises medicaments, which contain as active ingredients at least one compound of the general Formula (I), in which A is an unsubstituted phenyl group, or a pharmacologically usable addition salt thereof. These unsubstituted phenyl compounds are already known (Rink, Grabowski, Archiv. d.Pharmazie, 289, 1956, page 702), but their pharmacological properties have never been described. Their use in therapeutic treatment is therefore new, and medicaments which contain these compounds are also new.

The invention also relates to a method for preparing medicaments which contain at least one compound of Formula (I), or a compound of Formula (I) in which A is an unsubstituted phenyl group, or a pharmacologically usable acid addition salt thereof. This method comprises mixing the appropriate compounds with one or more inert, pharmacologically suitable carrier substances or adjuvants and of converting them in a known manner into galenical preparations. Such preparations may be, for example, tablets, dragees, capsules, powders, granulates, aqueous or oily suspensions, emulsions, syrups or solutions for oral administration, suppositories for rectal administration, suspensions for injection under sterile conditions, or solutions for parenteral administration.

The invention also provides a method of preparing a compound of Formula (I).

In a variant i), 17-hydroxyspartein or a 17-dehydrospartein salt, in particular the perchlorate, is reacted with a Grignard compound of Formula (III)

$$A—(CH_2)_n—MgHal \quad (III)$$

in which n is 0 or 1, A has the meaning given above under (a1), (a2), (b), (c1) to (c8), and Hal denotes halogen, in particular bromine or chlorine, to form the correspondingly substituted compound of Formula (I).

In a variant ii), a 17-dehydrospartein salt, in particular the perchlorate, is reacted with an organometallic compound of Formula (IV)

$$A—(CH_2)_n—Li \quad (IV)$$

in which n is 0 or 1 and A has the meaning given above under (a1), (b), (c1) to (c8), to form the correspondingly substituted compound of Formula (I).

The preparation of the compounds of Formulas (III) and (IV) is known and takes place by the reaction of a compound of Formula (VII)

$$A—(CH_2)_n—Hal \quad (VII)$$

with magnesium, lithium or with an alkyl lithium, preferably n-butyl-lithium. Hal represents halogen, in particular bromine or chlorine.

A compound of the Formula (IV) in which n=1 may also be produced from a compound of the Formula (VIII)

$$A—CH_3 \quad (VIII)$$

by deprotonating the activated methyl group attached to the aromatic ring with a strong base such as an alkyl lithium, preferably n-butyl lithium, or a lithium amide, preferably lithium diisopropyl amide. Activated methyl groups are contained, for example, in compounds of Formula (VIII) in which A is 2-pyridyl, 4-pyridyl, 2-(4,4-dimethyl-$\Delta^2$-oxazolino)-phenyl or phenyl substituted in position 2 or 4 by -CO-$R_4$, in which $R_4$ is substituted amino.

A compound of the Formula (IV) in which n=0 may also be obtained through direct deprotonation of activated ring hydrogen atoms from a compound of Formula (IX)

$$A—H \quad (IX)$$

by means of an alkyl lithium. Activated ring hydrogen atoms exist, for example, on the phenyl group in a position adjacent to an alkoxy-, preferably methoxy-, group, or in an alpha position of a furyl- or N-alkylpyrryl system.

The compounds of Formula (I) prepared in such a way may be obtained as such or in the form of their pharmacologically sable acid addition salts. However, they may also be further reacted to form other compounds of Formula (I) in accordance with the following variants:

In a variant iii) a compound, in which A is 2- or 4-bromophenyl or c2), is metalated with an alkyl lithium and is further reacted in a known manner to form a compound of Formula (I) in which A is (c1), (c3) to (c5) or (c10).

In a variant (iv) a compound, in which A is (c2), is reacted in a known manner to split off the alkoxy group and form a compound of Formula (I) in which A is (c9).

In a variant (v) a compound, in which A is (c8), is subjected to acid hydrolysis, to form the corresponding aldehyde.

The compounds resulting from variants (iii) to (v) may also be obtained as such or in the form of their pharmaceutically acceptable acid addition salts.

The organometallic reactions are carried out with the exclusion of moisture (using an absolute solvent) and atmospheric oxygen (under inert gas atmosphere, e.g. nitrogen or argon).

Suitable inert, organic solvents include ethers (e.g. diethylether, tetrahydrofuran, dioxane and dimethoxy ethane) or hydrocarbons (e.g. hexane, cyclohexane or benzene); preferred solvents being diethylether, tetrahydrofuran and hexane or mixtures thereof.

In variant (i), the Grignard reagent (III) is first produced from the corresponding halide (VII) and finely divided magnesium in accordance with the conditions of the Grignard reaction (e.g. K. Nuetzel, "Methoden zur Herstellung und Umwandlung magnesiumorganischer Verbindungen" ("Methods for the production and conversion of magnesium-organic compounds") in: Houben-Weyl, "Methoden der organischen Chemie" ("Methods of organic chemistry"), Vol. 13/2a, page 53 ff).

If necessary, a catalyst, such as iodine or 1,2-dibromoethane, may be used to produce the Grignard reagent. The reaction temperature usually lies between ambient temperature and the boiling point of the solvent or solvent mixture.

Depending upon the stearic and electronic properties of the halide (VII), the duration of the reaction may be from 30 minutes to several hours.

Alternatively, according to variant ii) an organolithium reaction may be carried out to produce the compound (I). The production of the lithium intermediate stage takes place according to standard methods (e.g. H. Gilman, "The Metalation Reaction with Organolithium Compounds", in: *Organic Reactions*, Vol. 8, page 258 ff, or H. R. Rodriguez, "Heteroatom Facilitated Lithiations", in *Orqanic Reactions*, Vol. 26, page 1 ff.), using for example reactants, such as metallic lithium, an alkyl lithium, such as for example n-butyl lithium, or a lithium amide such as lithium diisopropyl amide.

It is known that Lewis bases containing nitrogen increase the reactivity of the lithium compounds. Therefore, in an appropriate case a nitrogen containing Lewis base, such as for example N,N,N',N'-tetramethylethylene diamine (TMEDA) or 1,4-diazabicyclo-[2,2,2]octane (DABCO), may optionally be used as a catalyst.

The reaction may be carried out at a temperature from $-78°$ C. to $+40°$ C., and, depending upon the stearic and electronic properties of the halide (VII), the duration of the reaction may be from 30 minutes to several hours.

The phenyl lithium derivatives formed according to method variant (iii) by reaction of a bromide or alkoxy compound with an alkyl lithium, preferably n-butyl lithium, may be reacted in a known manner to form other new compounds of Formula (I) (e.g. N. S. Narasimhan, R. S. Mali, "Synthesis" 1983, page 957 ff). Examples of such reactions include reactions with N,N-dimethylformamide and alkyl halides.

The splitting off of the alkoxy radical according to variant (iv) takes place by known methods such as treatment with hydroiodic acid, boron tribromide, boron trichloride or phosphorus pentachloride, but preferably by treatment with hydroiodic acid.

The reactions may be carried out at normal (atmospheric) pressure, or at elevated pressure, but preferably at normal pressure, and the reaction temperatures may vary according to the method in a range from $-78°$ C. to $+200°$ C.

Any purification of the resulting compounds which may be necessary can be carried out in a conventional manner, e.g. through acid/base separation or by chromatographic methods.

The pharmaceutically acceptable acid addition salts which are obtainable according to the invention are obtained in the known manner by a reaction of the basic compounds (I) with acids which form pharmacologically usable salts.

The compounds of Formula (I) and their pharmacologically usable acid addition salts are distinguished by interesting pharmacological properties and show in particular oxygen-conserving effects, frequency-influencing effects, and rhythmizing effects on the heart. The new compounds are distinguished by a good efficacy and high tolerability.

Thus, the new compounds show even at low doses a marked lowering of heart frequency and also an additional antiarrhythmic effect. Moreover, the influence on the contractility of the heart tends to be positive. This means that the compounds have a particularly favorable relationship between their heart frequency lowering effect or extension of the refractory period of the heart and their inotropic effects, and consequently they have a broad therapeutic range.

The positive inotropic activity of the compounds of Formula I and the favorable combination of positive inotropic activity and heart frequency decreasing activity can be demonstrated in in vivo standard tests on animals, for example on rats. The positive inotropic effect can also be shown in vitro on isolated rat heart. The antiarrhythmic activity of the compounds can be demonstrated in vitro on the left auricles of guinea pig hearts.

Description of the Pharmacological Test Methods (1)
In vivo investigations on anesthetized rats.

The effect of the test substances on blood pressure and heart frequency in continuous i.v. infusions in anesthetized rats is determined by the method of Buschmann et al. (J. Cardiovascular Pharmacol., Vol. 2, pp. 777–781 (1980)).

Male Wistar rats (body weight 330–370 g) are anesthetized by i.p. administration of 1.25 g/kg urethane and tracheotomized. After an equilibration period of 10 minutes, the measurements are begun. The starting values are measured during a pre-test period of 5 minutes. The test substances are subsequently administered dissolved in isotonic sodium chloride solution (in appropriate cases with addition of a solvating agent) as continuous i.v. infusions, beginning with a dose of 0.01 $\mu$mole/kg/min. The dose is increased 10-fold every 10 minutes without increasing the infusion volume. A control group was administered solution free of active compound.

The influence of the test substances on the contracting force of the heart was investigated with regard to their effect on the maximum rate of increase of the arterial blood pressure of anesthetized rats. An increase in the maximum rate of increase of the arterial blood pressure is an indicator of an increase in the contracting force of the heart muscle and is therefore used as a parameter for investigating the contraction behavior (see Chan et al., J. Pharmacol. Methods, Vol. 18, pp 23–29, 1987). The maximum rate of increase in the pressure is derived from the blood pressure by electronic determination of the differential quotient $dP/dt_{max}$. In the following Table A1, the maximum effective dose is given as that dose at which the maximum rate of pressure increase $dP/dt_{max}$ reaches its highest value. In addition, the changes in the heart frequency and the average arterial blood pressure measured at this dose are listed. In each case the changes are given as net-percent values which are the changes measured at the respective dose and expressed in percent of the starting value minus the percent change measured at the same time in the control group. As can be seen from Table A1, the active compounds increase the $dP/dt_{max}$ and at the same time reduce the heart frequency with little or no effect on the average arterial blood pressure.

The example numbers given for the test compounds in Table A1 refer to the subsequent preparative examples (see Tables 2 through 5).

| Influence on the Maximum Rate of Increase of the Arterial Blood Pressure ($dP/dt_{max}$), Heart Frequency (FRQ) and Average Arterial Blood Pressure ($P_{av}$) | | | |
|---|---|---|---|
| Test Substance Ex. No. | Maximum Effective Dose μmole/kg i.v. | Net % Increase $dP/dt_{max}$ | Net % Change FRQ | Net % Change $P_{av}$ |
| 218 | 9.1 | 57 | −44 | +5 |
| 216 | 11 | 50 | −41 | +8 |
| 217 | 10 | 49 | −38 | +6 |
| 372 | 26 | 49 | −35 | −4 |
| 220 | 26 | 30 | −27 | +3 |
| 501 | 11 | 30 | −31 | +8 |
| 234 | 8.6 | 67 | −39 | +4 |
| 221 | 11 | 79 | −57 | −1 |
| 225 | 16 | 50 | −42 | −4 |
| 226 | 9.6 | 56 | −29 | +19 |
| 227 | 11 | 46 | −43 | −4 |
| 212 | 42 | 24 | −22 | −6 |
| 207 | 111 | 50 | −40 | −2 |
| 214 | 25 | 13 | −7 | −3 |
| 201 | 41 | 66 | −29 | +3 |

The influence of the active substance on the myocardial oxygen consumption of narcotized rats was also investigated in the same experimental model, and was calculated by the method of Neill (W. Z. Neill, H. H. Levine, R. J. Wagman, R. Gorlin, Circulation Research, Vol. 12, p. 163 (1963)). For this, the product of the of the systolic blood pressure and the heart frequency (=double product mm Hg . min$^{-1}$ . 0 01) is computed. The circulation measurements of systolic blood pressure and heart frequency which are necessary for this method were determined by the procedure of Buschmann et al., (G. Buschmann, W. Schumacher, R. Budden and U. G. Kuhl, "J. Cardiovasc. Pharmacol. 2" (1980), 777 to 795). As can be seen from the following Table A2, the active compounds decrease this double product of heart frequency and systolic blood pressure and thereby lead to a conservation of oxygen in the heart.

TABLE A2

| Influence on the Heart Frequency (FRQ), Systolic Blood Pressure ($P_s$) and the Double Product (DP) in Anesthetized Rats | | | | | |
|---|---|---|---|---|---|
| Test Substance Ex. No. | Dose μmole/kg i. v. | FRQ 1/min | $P_2$ mm Hg | DP mm Hg/ min · 100 | DP Change (percent) |
| 218* | pretest value | 368 | 123 | 453 | — |
|  | 6.6 | 254 | 124 | 312 | −29 |
| 221* | pretest value | 408 | 124 | 506 | — |
|  | 2.6 | 306 | 121 | 376 | −26 |

\* = utilized as the dihydrochloride

Following the method described above, the heart frequency reducing effect of the compounds listed in the following Table A3 was also determined. Table A3 lists the ED75%, which is the dose in μmoles/kg i.v. which produced a 25% reduction in the heart frequency to 75% of its pretest value. Further, the dose is also given at which the double product (DP) of the systolic blood pressure and the heart frequency decreases by 25% to 75% of its pretest value. The example numbers correspond to the numbers of the following examples or tables of examples.

TABLE A3

| Compound Example No. | FRQ ED75% μmole/kg i.v. | DP ED75% μmole/kg i.v. |
|---|---|---|
| 372 | 7.0 | 8.0 |
| 221 | 2.9 | 2.5 |
| 218 | 4.5 | 4.0 |
| 227 | 5.0 | 4.0 |
| 235 | 3.9 | 3.0 |
| 230 | 7.7 | 9.0 |
| 501 | 7.6 | 20 |
| 233 | 4.4 | 7.0 |
| 234 | 3.8 | 3.0 |
| 225 | 4.1 | 3.5 |
| 228 | 4.4 | 3.5 |
| 220 | 27 | 30 |
| 236 | 4.2 | 3.5 |
| 239 | 3.6 | 5.0 |
| 238 | 2.1 | 2.0 |
| 524 | 2.8 | 3.0 |
| 216 | 4.0 | 3.0 |
| 371 | 24 | 26 |
| 370 | 49 | 40 |
| 500 | 44 | 46 |
| 212 | 48 | 39 |
| 214 | 45 | 36 |
| 206 | 20 | 20 |
| 201 | 38 | 36 |
| 390 | 40 | 35 |
| 400 | 3.3 | 3.0 |
| 401 | 0.19 | 0.06 |

2. Determination of Minimum Toxic Dose

Male mice weighing 20–25 g were administered p.o. maximum doses of 300 mg/kg of the test compound. The animals were carefully observed for 3 hours for toxicity symptoms. Over a time period of 24 hours following the administration, all symptoms and deaths were additionally recorded. Side effects were likewise observed and recorded. If death or strongly toxic symptoms were observed, increasingly smaller doses were administered to additional mice until no more toxic symptoms occurred. The lowest dose which brought about death or strongly toxic symptoms is given as the minimum toxic dose in the following Table B.

TABLE B

| Compound Example No. | Minimum Toxic Dose mg/kg p.o. |
| --- | --- |
| 372 | >300 |
| 217 | 300 |
| 218* | 300 |
| 221* | 300 |
| 227** | >300 |
| 234** | >300 |
| 235** | 300 |
| 239 | 300 |
| 216** | >300 |
| 209 | >300 |
| 203 | 100 |
| 205 | >300 |
| 212 | 300 |

\* = utilized as the dihydrochloride
\*\* = utilized as the tartarate salt

3. In vitro Evidence of Antiarrhythmic Activity

Evidence of the antiarrhythmic effect of the active substances was obtained experimentally by determining the functional refractory period of the left auricle of the heart of female Albino Pirbright-white guinea pigs weighing 300 to 400 g by means of paired electrical stimulation following Govier's method (W. C. Govier, *J. Pharmacol. Exp. Ther.*, Vol. 148, No. 1, pp. 100–105 (1965)). In Table C, there is indicated as FRP 125% the concentration in μmole/l at which an extension of the functional refractory period to 125% occurs 18 minutes after administration of the test substance.

The direct influence of the active substance on heart frequency (FRQ) was tested on spontaneously beating, isolated right auricles of female Albino Pirbright-white guinea pigs weighing 300 to 400 g. In Table C the concentration in μmole/l at which a decrease of frequency to 75% of the initial value occurs 20 minutes after the substance is administered is indicated a FRQ 75%.

TABLE C

Influence on the Frequency (FRQ) of Spontaneously Beating Right Guinea Pig Auricles and on the Functional Refractory Period (FRP) of Electrically Stimulated Left Guinea Pig Auricles

| Test Substance of Formula I | Heart Affecting Characteristics Effective Concentration in μmole/l to achieve | |
| --- | --- | --- |
| Substance No.* | FRQ 75% | FRP 125% |
| 276*** | 1.46 | 3.52 |
| 217 | 4.69 | 3.71 |
| 218** | 2.06 | 6.24 |
| 221** | 0.99 | 2.17 |
| 225 | 4.09 | 2.83 |
| 227 | 5.12 | 2.47 |
| 234 | 3.13 | 2.58 |
| 235 | 1.9 | 3.24 |
| 239 | 0.95 | 2.69 |
| 372 | 4.85 | 3.39 |

*The compounds are used in the form (salt or free base) given in the tables of preparative examples unless otherwise indicated.
\*\* = Utilized as the dihydrochloride
\*\*\* = Utilized as the tartarate salt In this experimental model it is also apparent that the refractory period prolonging and thus antiarrhythmically effective characteristics of the active compounds of the invention also arise in the dose range of the heart frequency decreasing effect.

The compounds of the invention are characterized by a superior activity combination of oxygen-conserving, rhythmizing and frequency-influencing effects on the heart. This activity pattern enables them to be used in treating ischemic heart disease, e.g. angina pectoris and myocardial infarction, and also in treating life threatening arrhythmias. From the test results it is also clear that the compounds of Formula I have a marked positive inotropic activity in combination with a heart frequency decreasing activity, and thus they are especially suitable for treating heart failure, e.g. cases of insufficient heart pumping activity.

As active substances for treating cardiac insufficiencies and for producing pharmaceutical compositions with a positive inotropic effect, the compounds of Formula I can be used in the form of free bases or in the form of physiologically acceptable acid addition salts. The doses to be used may differ from individual case to case and naturally vary depending on the nature of the condition to be treated, the active substance used, and the manner of administration. For example, parenteral formulations generally contain less active substance than oral preparations. In general, however, satisfactory results may be obtained in animal experiments with doses of 0.01 to 100 mg/kg body weight. Medicinal compositions with an active substance content of from 0.5 to 50 mg, preferably 1 to 20 mg, of active substance per individual dose are suitable for administration to humans and large mammals.

In accordance with the invention, the compounds may be contained in solid or liquid pharmaceutical preparations together with conventional pharmaceutical adjuvants and/or carriers. Examples of solid preparations include orally administrable preparations such as tablets, capsules, powders, granules or dragees, or also suppositories. Solid preparations may include conventional pharmaceutical inorganic and/or organic carriers such as, for example, talcum, lactose, or starch in addition to conventional pharmaceutical adjuvants, for example lubricants or tablet decomposition agents. Liquid preparations such as solutions, suspensions or emulsions may contain the conventional diluents such as water, oils and/or suspending agents such as polyethylene glycols and the like. Further auxiliary agents may be added supplementally such as, for example, preservatives, taste improving agents, and the like.

The active substance may be mixed and formulated with the pharmaceutical adjuvants and/or carriers in a known manner. To produce solid pharmaceutical compositions, the active substance may, for example, be mixed with the adjuvants and/or carriers in the usual manner and wet or dry granulated. Depending on the type of auxiliary agents used, a directly tabletable powder may be obtained in some cases by simple mixing. The granulate or powder may be filled directly into capsules or pressed in the usual manner into tablet cores. If desired, these can be formed in a known manner into dragees.

The compounds and pharmaceutical compositions of the invention are useful to treat various types of heart conditions according to the methods of the invention. For example, they may be used to treat ischemic heart conditions which comprise an imbalance between the supply of oxygen available to the heart (cardiac oxygen supply) and the demand for oxygen in the heart (cardiac oxygen demand). Functional consequences of such imbalances may include angina pectoris and/or heart rhythm disturbances. The compounds and compositions of the invention act to restore a balance between the oxygen supply and the oxygen demand by increasing the oxygen supply and/or by decreasing the oxygen demand through a decrease in the heart rate. Due to their pronounced antiarrhythmic activity they may also be used to treat heart rhythm disorders arising from any other cause. Similarly, due to their positive inotropic activity, they may be used to treat instances of heart failure, i.e. insufficient pumping action by the heart, by improving the contractility of the heart muscle.

The following Examples are intended to explain the preparation of the new compounds of Formula (I) in greater detail, but not to restrict the scope of the invention in any way.

The structures of the new compounds were established by spectroscopic investigations, in particular by analysis of the NMR-, mass-, IR- and/or UV- spectra.

The 17-hydroxyspartein was obtained from spartein in accordance with DE-OS 28 25 117.

The 17-dehydrospartein perchlorate was produced from 17-hydroxyspartein in accordance with M. Rink and K. Grabowski, "Arch. Pharm.", 289, (1965) 695.

The following abbreviations are used in the Examples and Tables:
SOL=solvent,
THF=tetrahydrofuran,
Et=diethyl ether,
T=temperature (.C),
Cat=catalyst,
P=17-dehydrosparteinperchlorate,
H=17-hydroxyspartein,
DBE=1,2-dibromoethane,
TS=tartaric acid salt,
HFu=fumaric acid salt.

EXAMPLE 1

Preparation of Compounds of Formula (III) or Formula (IV)

(1a) Preparation of compounds of Formula (III)

0.1 mole Magnesium chips are placed in 50 ml absolute solvent. If required, catalyst is added. After the dropwise addition of 0.1 mole of compound of Formula (VII) in 50 ml solvent, the formulation is kept at reflux until the magnesium is dissolved. The reaction mixture is used as such for the reaction in Example 2.

(1b) Preparation of compounds of Formula (IV)

4.4 mmole n-butyl lithium (as a 15% solution in hexane) are dissolved in 30 ml absolute solvent at −78° C. After the slow dropwise addition of 4.5 mmole of compound of Formula (VII) in 30 ml solvent, stirring takes place for a further 30 minutes at −78° C. This reaction mixture is used for the reaction in Example 3.

(1c) Preparation of compounds of Formula (IV)

0.1 mole of a compound of Formula (VIII) is added dropwise to a solution of 0.1 mole lithiumdiisopropylamide produced in situ from diisopropylamine and n-butyl lithium - in 100 ml absolute solvent at a corresponding temperature, and stirred. Thereafter, the mixture is diluted with 200 ml solvent, and the resulting reaction mixture is used for the reaction in Example 3.

(1) Preparation of compounds of Formula (IV)

62.5 ml of a 1.6 molar solution of n-butyl lithium in hexane are added dropwise to 0.1 mole of a compound of Formula (IX) in 50 ml solvent, optionally in the presence of an approximately equimolar quantity of catalyst, under cooling (T1). In order to complete the deprotonation, the reaction mixture is stirred further at an elevated temperature (T2). The resulting reaction mixture is used for the reaction in Example 3, whereby the temperature is previously adjusted to T3.

Details regarding particular reaction conditions for the synthesis of individual compounds can be found in Tables 1a) to 1d).

TABLE 1a

Preparation of compounds of Formula (III) from compounds of Formula (VII)

| Example | SOL | Cat | A | n | Hal |
|---|---|---|---|---|---|
| 100 | THF | — | 2-thienyl | 0 | Br |
| 101 | Et | iodine | phenyl | 0 | Br |
| 102 | Et | iodine | 2-methoxy-phenyl | 0 | Br |
| 103 | Et | iodine | 3-methoxy-phenyl | 0 | Br |
| 104 | Et | iodine | 4-methoxy-phenyl | 0 | Br |
| 105 | Et | iodine | 3,4-methylene dioxylphenyl | 0 | Br |
| 106 | Et | iodine | 3,4-ethylene dioxyphenyl | 0 | Br |
| 107 | Et | iodine | 2-trifluoromethylphenyl | 0 | Br |
| 108 | Et | iodine | 3-trifluoromethylphenyl | 0 | Br |
| 109 | Et | iodine | 4-trifluoromethylphenyl | 0 | Br |
| 110 | Et | iodine | 3-chlorophenyl | 0 | Br |
| 111 | Et | iodine | 4-chlorophenyl | 0 | Br |
| 112 | Et | iodine | 3-fluorophenyl | 0 | Br |
| 113 | Et | iodine | 4-fluorophenyl | 0 | Br |
| 114 | THF | $CH_3I$ | 3,4-dimethoxyphenyl | 0 | Br |
| 115 | THF | $OCl_4$ | 3-methylphenyl | 0 | Br |
| 116 | THF | | phenyl | 1 | Cl |
| 117 | Et | iodine | 2-methxoyphenyl | 1 | Cl |
| 118 | Et | iodine | 3-methoxyphenyl | 1 | Cl |
| 119 | Et | iodine | 4-methoxyphenyl | 1 | Cl |
| 120 | THF | DBE | 3,4,5-trimethoxyphenyl | 1 | Cl |
| 121 | Et | iodine | 2-chlorophenyl | 1 | Cl |
| 122 | Et | iodine | 3-chlorophenyl | 1 | Cl |
| 123 | Et | — | 4-chlorophenyl | 1 | Br |
| 124 | Et | — | 3-trifluoromethlyphenyl | 1 | Cl |
| 125 | Et | — | 2-fluorophenyl | 1 | Br |
| 126 | Et | — | 3-fluorophenyl | 1 | Br |
| 127 | Et | — | 4-fluorophenyl | 1 | Br |
| 128 | Et | — | 2-bromophenyl | 1 | Br |
| 129 | Et | DBE | 3-bromophenyl | 1 | Br |
| 130 | Et | DBE | 4-bromophenyl | 1 | Br |
| 131 | Et | — | 3,4-dichlorophenyl | 1 | Br |
| 132 | Et | — | 2,6-dichlorophenyl | 1 | Br |
| 133 | Et | — | 2-methlyphenyl | 1 | Br |
| 134 | Et | — | 3-methlyphenyl | 1 | Br |
| 135 | Et | — | 4-methlyphenyl | 1 | Br |
| 136 | Et | — | 2,4-dimethlyphenyl | 1 | Cl |
| 137 | Et | — | 3,5-dichlorophenyl | 1 | Cl |
| 138 | Et | — | 2,6-difluorophenyl | 1 | Br |
| 139 | Et | — | 2-fluoro-3-methylphenyl | 1 | Br |
| 140 | Et | — | 2-chloro-6-fluorophenyl | 1 | Cl |

TABLE 1b

Preparation of compounds of Formula (IV) from compounds of Formula (VII)

| Example | SOL | A | n | Hal |
|---|---|---|---|---|
| 150 | THF | 2-pyridyl | 0 | Br |
| 151 | Et | 4-bromophenyl | 0 | Br |

TABLE 1c

Preparation of compounds of Formula (IV) from compounds of Formula (VIII)

| Example | SOL | T | A | n |
|---|---|---|---|---|
| 170 | THF | −78 | 4-pyridyl | 1 |
| 171* | THF | −78 | 2-pyridyl | 1 |
| 172** | THF | 0 | 2,3-dimethoxyphenyl | 1 |
| 173 | THF | 0 | 4,N,N—diisopropylbenzamide | 1 |
| 174* | Et | 0 | 2-(4,4-dimethyl-$\Delta^2$-oxazolino)-phenyl | 1 |

Note:
* = n-butyl lithium in place of diisopropylamide
** = with the addition of TMEDA

TABLE 1d
Preparation of compounds of Formula (IV) from compounds of Formula (IX)

| Example | SOL | CAT | T₁ °C. | T₂ °C. | T₃ °C. | A | n |
|---|---|---|---|---|---|---|---|
| 190 | THF | — | −25 | −15 | 0 | 2-furyl | 0 |
| 191 | THF | TMEDA | 0 | +40 | −30 | 2-(N—methyl)pyrryl | 0 |

EXAMPLE 2

Preparation of a compound of Formula (I) according to Variant (i)

0.005 mole 17-hydroxyspartein or 17dehydrospartein-perchlorate in 100 ml solvent are added to the reaction mixture derived from Example (1a) and heated under reflux up to complete reaction. After careful acidification with dilute hydrochloric acid and subsequent acid/base separation and chromatography on neutral aluminum oxide or silica gel with an ether/hexane mixture as a mobile solvent, the compound of Formula (I) is isolated. If desired, this compound may be converted into its acid addition salt. Particular reaction conditions for the preparation of individual compounds and the physical data of the resulting products are shown in Table 2.

EXAMPLE 3

Preparation of a compound of Formula (I) according to Variant (ii)

(3a) An equimolar quantity of solid 17-dehydrospartein-perchlorate was added to the reaction mixture obtained from Example (1b) or (1c) (1d) and was further stirred with slow heating to ambient temperature to complete the reaction.

After addition of dilute acid or ice-water, the reaction mixture obtained from Example (1b) or (1c) or (1d) and was further stirred with slow heating to ambient temperature to complete the reaction.

After addition of dilute acid or ice-water, the reaction mixture was worked up as in Example 2. Details regarding particular reaction conditions and products obtained are given in Table 3.

(3b) Seven ml of N,N,N',N'-tetramethylethylenediamine were added to 9.2 g of 2,3-dimethoxytoluene in 50 ml of absolute tetrahydrofuran at −75° C. Thereafter 37.6 ml of a 1.6 molar solution of n-butyllithium in hex-

TABLE 2
Preparation of compounds of Formula (I) according to Variant (i)

| Example | Spartein derivative | SOL | A | n | isolated form | MP °C. |
|---|---|---|---|---|---|---|
| 200 | P | THF | 2-thienyl | 0 | base | 84 |
| 201 | H | Et | phenyl | 0 | base | 105–107 |
| 202 | P | Et | 2-methoxyphenyl | 0 | 2 HCl | 220 |
| 203 | P | Et | 3-methoxyphenyl | 0 | 2 HCl | 208 |
| 204 | P | Et | 4-methoxyphenyl | 0 | 2 HCl | 238 |
| 205 | P | Et | 3,4-methylene dioxyphenyl | 0 | 2,33 TS | 145 |
| 206 | P | Et | 3,4-ethylenedioxyphenyl | 0 | 1,9 HFu | 187 |
| 207 | P | Et | 2-trifluoromethylphenyl | 0 | base | 130 |
| 208 | H | Et | 3-trifluoromethylphenyl | 0 | 2 HCl | amorphous |
| 209 | H | Et | 4-trifluoromethylphenyl | 0 | 2 HCl | amorphous |
| 210 | H | Et | 3-chlorophenyl | 0 | 3 TS | amorphous |
| 211 | H | Et | 4-chlorophenyl | 0 | 3,4 TS | amorphous |
| 212 | H | Et | 3-fluorophenyl | 0 | 3 TS | amorphous |
| 213 | H | Et | 4-fluorophenyl | 0 | 3,6 TS | amorphous |
| 214 | P | THF | 3,4-dimethoxyphenyl | 0 | base | 117 |
| 215 | P | THF | 3-methylphenyl | 0 | 2,3 HFu | amorphous |
| 216 | P | THF | phenyl | 1 | base | 68–71 |
| 217 | P | Et | 2-methoxyphenyl | 1 | base | 59 |
| 218 | P | Et | 3-methoxyphenyl | 1 | base | 51–52 |
| 219 | H | Et | 4-methoxyphenyl | 1 | base | 100 |
| 220 | P | THF | 3,4,5-trimethoxyphenyl | 1 | 2,8 TS | 103 |
| 221 | H | Et | 2-chlorophenyl | 1 | base | 115 |
| 222 | H | Et | 3-chlorophenyl | 1 | base | 76 |
| 223 | P | Et | 4-chlorophenyl | 1 | base | 120 |
| 224 | H | Et | 3-trifluoromethylphenyl | 1 | 2,8 HFu | amorphous |
| 225 | P | THF | 2-fluorophenyl | 1 | 2,25 TS | 126 |
| 226 | P | THF | 3-fluorophenyl | 1 | 2,15 TS | 138 |
| 227 | P | THF | 4-fluorophenyl | 1 | base | 74 |
| 228 | P | THF | 2-bromophenyl | 1 | base | 131 |
| 229 | P | THF | 3-bromophenyl | 1 | 2 TS | 138–140 |
| 230 | P | THF | 4-bromophenyl | 1 | base | 142 |
| 231 | P | THF | 3,4-dichlorophenyl | 1 | base | 80 |
| 232 | P | THF | 2,6-dichlorophenyl | 1 | 2,1 TS | 143 |
| 233 | P | THF | 2-methylphenyl | 1 | 2,1 TS | 140 |
| 234 | P | THF | 3-methylphenyl | 1 | base | 57 |
| 235 | P | THF | 4-methylphenyl | 1 | base | 58 |
| 236 | P | THF | 2,4-dimethylphenyl | 1 | base | 158–161 |
| 237 | P | THF | 3,5-dichlorophenyl | 1 | 2,1 TS | 130 |
| 238 | P | THF | 2,6-difluorophenyl | 1 | 2,2 TS | 135 |
| 239 | P | THF | 2-fluoro-3-methylphenyl | 1 | 2,1 TS | 139 |
| 240 | P | THF | 2-chloro-6-fluorophenyl | 1 | 2,2 TS | 131 | ame were added dropwise at this temperature. After the addition was completed, the temperature of the reaction mixture was slowly brought to 0° C.

To the resulting reaction mixture were added 10 g of solid 17-dehydrospartein-perchlorate. The solution was allowed to warm slowly to room temperature while stirring was continued until the reaction was complete. Subsequently, the product compound of Formula I was isolated as described in Example 2. The resulting 17-(2,3-dimethoxybenzyl)-spartein hydrochloride obtained as a colorless oil can be converted into an amorphous hydrochloride with an ether solution of HCl.

EXAMPLE 4

Preparation of a compound of Formula (I) according to Variant (iii)

0.013 mole educt were dissolved in absolute solvent with catalyst being added if required. Under cooling, 0.02 mole n-butyl lithium (as a 15% solution in hexane) were added dropwise and, after stirring at ambient temperature for 1 to 6 hours, 0.04 mole N,N-dimethylformamide in 20 ml solvent were added. After completion of the reaction, water was added, and the reaction mixture was worked up as in Example 2. Particular reaction conditions and products obtained are listed in Table 4.

EXAMPLE 5

Preparation of a compound of Formula (I) according to Variant (iv)

30 ml 57% hydroiodic acid were added slowly dropwise to 0.017 mole educt in 14 ml acetic anhydride. The formulation was heated under reflux for 4 hours. The reaction mixture was carefully introduced into icewater and was worked up as indicated under Example 2. Details regarding reaction conditions and products obtained are shown in Table 5.

EXAMPLE 6

Preparation of a compound of Formula (I) according to Variant v)

0.02 mole magnesium were placed in 50 ml absolute THF. After activation with 2.0 ml 1,2-dibromoethane, 0.02 mole 2-(3-bromophenyl)-1,3-dioxolane in 10 ml absolute THF are added dropwise. After the formulation has been heated for 1 hour at reflux, it was diluted with 100 ml absolute THF and mixed with 0.01 mole 17-dehydrospartein perchlorate, and reheated to complete the reaction.

In order to form the free aldehyde, the reaction solution was mixed with dilute hydrochloric acid and stirred for 30 minutes at ambient temperature. After acid/base separation and subsequent filtration over alumina with ether/hexane (1:1) as mobile solvent, the formyl derivative can be isolated as an oil. By reaction with three equivalents of tartaric acid, a crystalline tartrate was obtained (melting point: 126° to 130° C.).

EXAMPLE 7

Splitting of the Ether to Produce a Hydroxy Derivative

Thirty ml of 57% solution of hydrogen iodide were permitted to drip slowly into 0.017 mole of 17-(3methoxybenzyl)-spartein in 14 ml of acetic anhydride. The reaction mixture was heated at reflux for 4 hours and then poured carefully onto ice water. An acid-base separation was then carried out. The resulting 17-(3-hydroxybenzyl)-spartein had a melting point of 74°-76° C.

The following Example 8 through 12 describe pharmaceutical preparations containing the active substance according to the invention and also the production of such pharmaceutical preparations.

TABLE 3

Preparation of compounds of Formula (I) according to Variant (ii)

| Example | Formulation | n | A | isolated form | MP °C. |
|---|---|---|---|---|---|
| 350 | 1b | 0 | 2-pyridyl | 2 TS | 135 |
| 351 | 1b | 0 | 4-bromophenyl | 2,3 TS | 150 |
| 370 | 1c | 1 | 4-pyridyl | 3 TS | 120 |
| 371 | 1c | 1 | 2-pyridyl | base | 128 |
| 372 | 1c | 1 | 2,3-dimethoxyphenyl | 2 HCl | amorphous |
| 373 | 1c | 1 | 4-N,N—diisopropylamino-carbonylphenyl | 2,5 TS | 145–148 |
| 374 | 1c | 1 | 2-(4,4-dimethyl-Δ²-oxazolino)-phenyl | base | 112–119 |
| 390 | 1d | 0 | 2-furyl | 2,5 TS | 113 |
| 391 | 1d | 0 | 2-(N—methyl)-pyrryl | base | 118 |

TABLE 4

Preparation of compounds of Formula (I) according to Variant (iii)

| Example | Educt | SOL | Cat | T | A | n | isolated form | MP °C. |
|---|---|---|---|---|---|---|---|---|
| 400 | 218 | THF | TMEDA | 0 | 3-methoxy-4-formyl- | 1 | 2,3 TS | 117–120 |
| 401 | 351 | THF | — | −30 | 4-formyl-phenyl | 0 | base | 106 |

TABLE 5

Preparation of compounds of Formula (I) according to Variant iv

| Example | Educt | A | n | isolated form | MP° C. |
|---|---|---|---|---|---|
| 500 | 204 | 4-hydroxyphenyl | 0 | 2 HCl | amorphous |
| 501 | 218 | 3-hydroxyphenyl | 1 | base | 74–76 |

EXAMPLE 8—TABLETS

| Composition: | |
|---|---|
| Active substance (Example 2, No. 218) | 20 parts |
| Corn Starch | 30 parts |
| Lactose | 55 parts |
| Polyvinyl pyrrolidone | 5 parts |
| Magnesium stearate | 2 parts |
| Hydrogenated castor oil | 1 part |

-continued

| Composition: | |
|---|---|
| Total | 113 parts |

Directions for preparation:

The active substance is mixed with the corn starch and lactose powder in a mixer. The resulting mixture is thoroughly moistened with a 20% solution of polyvinyl pyrrolidone (Kollidon 25 ™ from BASF) in isopropanol. If required, further isopropanol is added. The moist granulate is passed through a 2 mm screen, dried at 40° C. on latticed screens and is then passed through a 1 mm screen (Frewitt machine). After mixing castor oil, tables of 113 mg are formed by pressing so that each tablet contains 20 mg of active substance.

EXAMPLE 9—CAPSULES

| Composition | |
|---|---|
| Active substance (Example 2, No. 218) | 20 parts |
| Corn starch | 20 parts |
| Lactose | 45 parts |
| Polyvinyl pyrrolidone | 3 parts |
| Magnesium stearate | 1.5 parts |
| Silica aerogel | 0.5 part |
| Total | 90 parts |

Directions for preparation:

The active substance is mixed with corn starch and lactose powder in a mixer. The resulting mixture is thoroughly moistened with a 20% solution of polyvinyl pyrrolidone (Dollidon 25¾ from BASF) in isopropanol. If required, further isopropanol is added. The moist granulate is passed through a 1.6 mm screen (Frewitt), dried at 40° C. on latticed screens and is then passed through a 1 mm screen (Frewitt). After the mixing of the granulate with magnesium stearate and lilica aerogel (Aerosil 200 ™ from DEGUSSA), 90 mg portions thereof are filled by means of an automatic capsule machine into size 4 hard gelatine capsules so that each capsule contains 20 mg active substance.

EXAMPLE 10—CAPSULES

The procedure of Example 9 was repeated except 55 parts of lactose and only 10 parts of active compound were used to produce capsules each containing 10 mg of active substance.

EXAMPLE 11—AMPOULES

| Composition (per ampoule): | |
|---|---|
| Active substance (Example 2, No. 218) | 5 mg |
| Sodium chloride | 16 mg |
| Water for injection purposes ad | 2.0 ml |

Directions for preparation:

The sodium chloride is dissolved in water for injection purposes, the active substance is added and dissolved under stirring. Filling takes place up to the final volume with sufficient water for injection purposes. The formulation is passed through a 0.25 μ membrane filter. Brown glass ampoules are each filled with 2.15 ml and are sealed by melting. Sterilization with steam is carried out at 121° C. for 30 minutes. 2 ml injection solution contain 5 mg active substance.

EXAMPLE 12—AMPOULES

The procedure of Example 11 was repeated except only 2 mg of active compound were used to produce 2 ml of an injectable solution so that each ml contained 1 mg of active substance.

What is claimed is:

1. A method of treating a heart condition in a mammal comprising the step of administering to said mammal an effective heart condition improving amount of a spartein derivative corresponding to the Formula (I)

$$S-(CH_2)_n-A \quad (I)$$

in which
S is a 17-spartein nucleus
n is 0 or 1, and
A is 2-furyl, 2-thienyl or 2-(N-loweralkyl)-pyrryl when n=0, or 3-furyl or 3-thienyl when n=1, or pyridyl, or
a phenyl group of the Formula (II)

$$\text{(II)}$$

in which $R_1$, $R_2$ and $R_3$ are individually selected from the group consisting of hydrogen, lower alkyl containing 1 to 4 carbon atoms, lower alkoxy containing 1 to 4 carbon atoms, chlorine, flourine, fromine trifluoromethyl, $$-CH-O-(CH_2)_2-O,$$

hydroxy, or $-CO-R_4$ in which $R_4$ is hydrogen, lower alkoxy containing 1 to 4 carbon atoms, hydroxy, amino or mono-or di- lower alkyl substituted amino, or two adjacent ones of $R_1$, $R_2$ and $R_3$ together form an alkylene dioxy group containing 1 or 2 carbon atoms; or a pharmaceutically acceptable acid addition salt thereof.

2. A method according to claim 1, wherein A is a phenyl group of the Formula (II)

$$\text{(II)}$$

wherein $R_1$, $R_2$ and $R_3$ have the meanings set forth in claim 1.

3. A method according to claim 2, wherein n=1.

4. A method according to claim 2, wherein at least one of $R_1$, $R_2$ and $R_3$ is hydrogen.

5. A method according to claim 1, wherein A represents a phenyl group of the Formula (II)

$$\text{(II)}$$

in which $R_1$, $R_2$ and $R_3$ are individually selected from the group consisting of hydrogen, lower alkyl, lower alkoxy, chlorine fluorine, brominl, trifluoromethyl and hydroxy.

6. A method according to claim 5, wherein 7. a method according to claim 1, wherein $R_1$ is selected from the group consisting of hydrogen, florine, chlorine, hydroxy, lower alkoxy and lower alkyl; $R_2$ is hydrogen or if $R_1$ is lower alkoxy, $R_2$ may also be lower alkoxy; and $R_3$ is hydrogen or $R_1$ and $R_2$ are lower alkoxy, $R_3$ may also be lower alkoxy.

8. A method according to claim 6, wherein said spartein derivative is 17-(3-methoxybenzyl)-spartein or a pharmaceutically acceptable acid addition salt thereof.

9. A method according to claim 1, wherein said heart condition is an ischemic heart condition comprising an imbalance between cardiac oxygen supply and cardiac oxygen demand, and said method comprises administering to said mammal suffering from said ischemic heart condition an amount of said spartein derivative effective to restore a balance between cardiac oxygen supply and cardiac oxygen demand.

10. A method according to claim 1, wherein said heart condition comprises a disturbance of cardiac rhythm, and said method comprises administering to said mammal suffering from said cardiac rhythm disturbance an antiarrhythmically effective amount of said spartein derivative.

11. A method according to claim 1, wherein said heart condition comprises inadequate pumping function of the heart, and said method comprises administering to said mammal suffering from said inadequate pumping function a positive inotropically effective amount of said spartein derivative.

* * * * *